United States Patent [19]

Matteucci

[11] Patent Number: 4,923,808

[45] Date of Patent: May 8, 1990

[54] METHOD FOR IDENTIFYING MUTANTS SECRETING HIGH LEVELS OF HETEROLOGOUS PROTEINS

[75] Inventor: Mark D. Matteucci, San Francisco, Calif.

[73] Assignee: Genentech, Inc., South San Francisco, Calif.

[21] Appl. No.: 220,901

[22] Filed: Jul. 18, 1988

Related U.S. Application Data

[63] Continuation of Ser. No. 711,127, Mar. 12, 1985, abandoned.

[51] Int. Cl.$^5$ ............................................. C12N 9/00
[52] U.S. Cl. ................................................. 435/69.8
[58] Field of Search ................... 435/4, 18, 21, 68, 70, 435/71, 91, 172.1, 172.3, 253, 320, 183, 196, 252.3, 252.31–252.35; 935/47, 48, 79, 82, 76, 14

[56] References Cited

U.S. PATENT DOCUMENTS 4,356,270 10/1982 Itakura ................................. 435/320
4,425,437 1/1984 Riggs .................................... 435/320

FOREIGN PATENT DOCUMENTS 2071671 9/1981 United Kingdom ............. 435/172.3

OTHER PUBLICATIONS

Koshland et al., *Cell,* 30: 903–914 (Oct. 1982).
Wright et al., *J. Cell Biochem,* Suppl. 7B: 346 (1983), Ab. 1408.
Villa—Komaroff et al.; Proc. Natl. Acad. Sci. U.S.A. 75: 3727 (1978).
Fognini—Lefebvre et al.; Chem. Abstr. 99: 191270q (1983).
Lazzaroni et al.; J. Bacteriol. 145: 1351 (1981).

*Primary Examiner*—James Martinell

[57] ABSTRACT

A method is provided for identifying mutants that leads to the enhanced expression and periplasmic secretion of heterologous preproteins from host cells. Mutants in the host cell or in the gene encoding the heterologous preprotein are identified readily by transforming the host cell with a fusion which comprises DNA encoding the heterologous preprotein and a detectable marker protein. A marker protein is chosen that only becomes active in the periplasmic or extracellular environment. Thus, desired mutants are identified by enhanced marker expression and secretion. The ability of the preprotein DNA or host cell mutants to enhance expression and secretion of the heterologous protein-enzyme fusions is found to correlate with similar enhancement of the expression and secretion of the heterologous protein alone and not as a fusion. Screening assays led to the identification of a preprotein silent mutation resulting in high-yield secretion that could not be explained under current theories and which provides a new method for obtaining high-yielding host-vector systems.

11 Claims, 1 Drawing Sheet

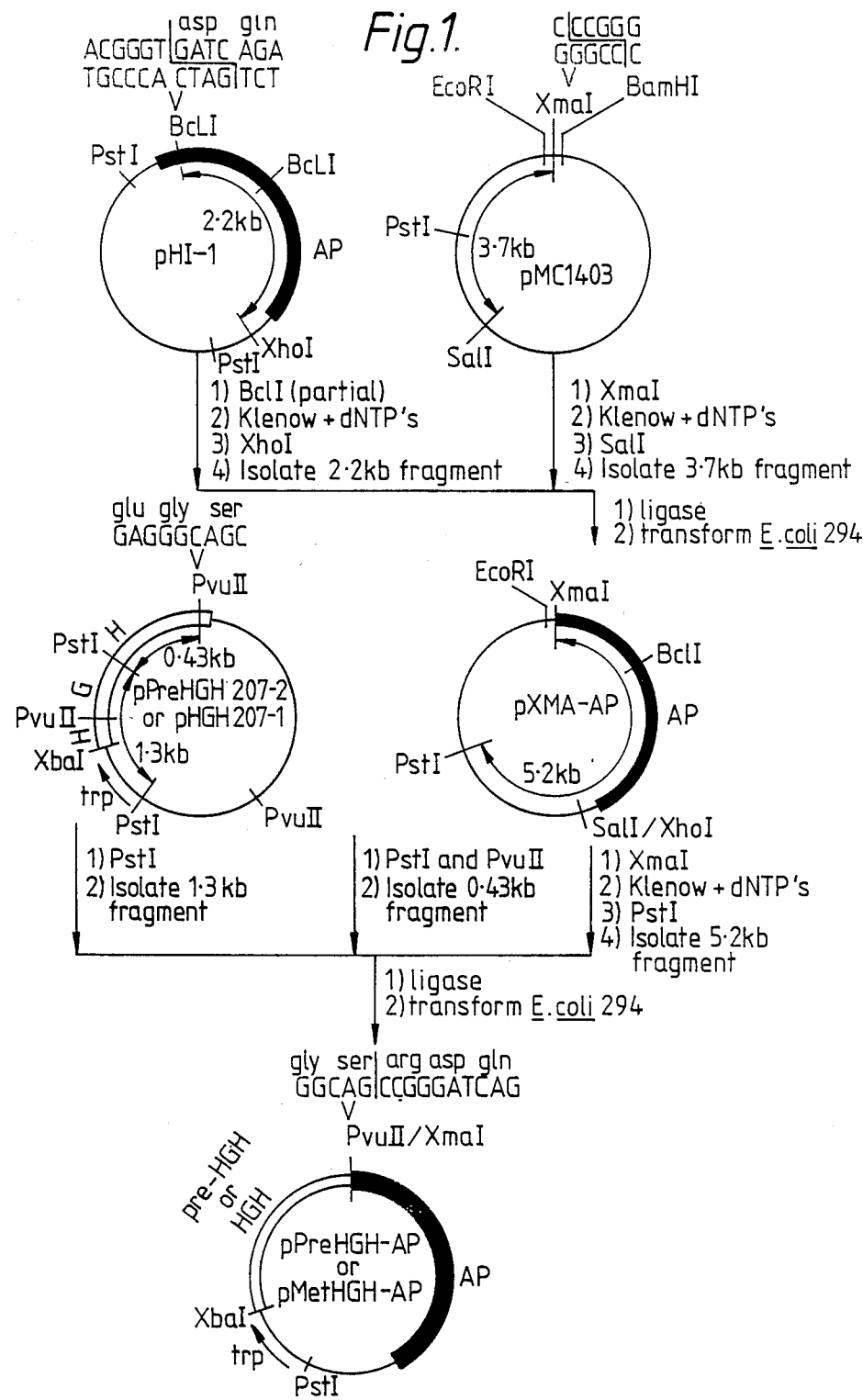

METHOD FOR IDENTIFYING MUTANTS SECRETING HIGH LEVELS OF HETEROLOGOUS PROTEINS

This is a continuation of Ser. No. 711,127, filed March 12, 1985, now abandoned.

BACKGROUND

Gene fusions with β-galactosidase (β-gal) have been used to monitor gene expression in *E. coli* (1, 2, 3, 32). Such fusions have been used with limited success in the study of secretory proteins. β-gal fusions of such proteins can be lethal to the host and in cases of nonlethality the β-gal is active whether it remains cytoplasmic or is secreted to the periplasmic space (4).

Alkaline phosphatase (AP) has been shown to have enzymatic activity when it is secreted to the periplasm (5). This activity can be visually estimated by the intensity of the blue color of colonies grown on agar plates containing 5-Bromo-4-chloro-3-indolyl phosphate (X-P) (6). Wright has shown examples where gene fusions at the amino terminus of AP preserved enzymatic activity and that the first 33 amino acids of the amino terminus of AP were not required for activity (7). Additionally, AP can be secreted to the periplasm at a high level in *E. coli* when carried on a multicopy plasmid (6). In this connection see European Patent Application 77,569.

Methods are known for the secretion of heterologous proteins into bacterial periplasmic space (33, 34). However, no convenient methods are available to the art which would facilitate the screening of large numbers of transformants in order to identify host cells or vector constructions that secrete high levels of desired protein. Instead, each transformant has been cultured individually, periplasmic product recovered and the efficacy of the host-vector system evaluated by product assays.

Accordingly, it is an object of this invention to provide a method for screening transformants to identify those having the ability to secrete maximal levels of heterologous protein.

It is a further object herein to provide a method for rapidly and economically identifying mutants within the coding and noncoding regions of the DNA to be expressed which enhance the expression and/or secretion of the desired heterologous protein, as well as mutants in the host cell which exert a similar effect.

These and other objects will be apparent to the ordinary artisan from consideration of the specification as a whole.

SUMMARY

The objects of this invention are accomplished by a method comprising (a) providing a replicable expression vector comprising nucleic acid that encodes a marker protein and nucleic acid comprising a preprotein gene, said marker protein being capable of undergoing a detectable change upon secretion from the host cell, and said marker protein and preprotein being capable of expression and secretion under common control; (b) introducing a mutation into the preprotein gene; (c) transforming a host cell with the vector of step (b) wherein the mutated preprotein gene of step (b) is heterologous; and (d) assaying the transformed host cell for a change which occurs in the marker protein upon secretion.

Quantitative assays for the secretory modification in the marker protein enable one to identify productive secretory mutants. Thereafter, the host cells are transformed with a vector devoid of functional marker protein nucleic acid but which contains the high-yielding mutant gene encoding the heterologous protein. For example, this vector is made by deleting the marker protein coding region from the nucleic acid encoding the fusion and the resulting vector repaired in order to encode the complete heterologous protein. Such vectors transform the host cells to express the mature heterologous protein without marker protein contamination while still retaining the productive character of the mutant.

A silent mutant was identified by this method that produced the best yields, thereby providing a basis for screening silent mutations for elevated yield, even though the mutations are not expected to produce such results based on presently known theories.

BRIEF DESCRIPTION OF THE DRAWING

FIG. 1 depicts the construction of the HGH-AP fusion plasmids pPreHGH-AP and pMetHGH-AP. HGH is an abbreviation for human growth hormone.

DETAILED DESCRIPTION

The marker protein used herein is a phenotypic tag which optimally will be detectable by color or fluorescence changes in a culture medium upon which transformant colonies can be grown, or which enables the survival of only those transformants that secrete the marker. Intracellular expression of the marker will be by definition insufficient to confer on the host cell the detectable change in phenotype. In other words, the marker is selective for secretion of the fusion protein.

The marker protein generally is an enzyme which is active only after secretion from the transformed cell into the periplasmic space or the surrounding culture medium. This result is achieved, for example, by the cytoplasmic expression of the marker as an inactive proenzyme or zymogen, which in turn is activated only by substances such as other enzymes or conditions found in the extracytoplasmic environment. Examples include alkaline phosphatase and β-lactamase. The preferred embodiment is alkaline phosphatase. The gene encoding *E. coli* alkaline phosphatase is publicly described (6) or may be synthesized from the known alkaline phosphatase DNA sequence (35).

The marker protein will only function as such if its secretion parallels that of the heterologous preprotein mutant. Thus under ordinary circumstances the marker protein or an effective fragment thereof will be present as a fusion to the carboxy terminus of at least a portion of the heterologous protein gene. Thus the ultimate expression and secretion of the heterologous protein and the marker in the fusion is under the common control of the same promoter, Shine-Dalgarno and signal sequence.

The amount of DNA encoding heterologous protein and marker polypeptide which is present in the DNA encoding the fusion is not critical. All that is necessary is that sufficient DNA be present to encode a fusion which retains the key capabilities of the marker polypeptide, i.e. the fusion polypeptide must undergo a detectable change upon secretion. This will depend upon the marker protein and the domains thereof required to undergo the change, and will accordingly vary for each marker polypeptide. Generally the portion of heterologous protein present in the fusion will encompass about from the first 5 to the first 50 residues thereof. DNA comprising the coding DNA for the entire mature heterologous protein can be ligated to the mature amino terminus of the marker polypeptide in some embodiments.

Note that heterologous is defined in terms of the host cell per se, and not the strain, species or genus to which the host belongs. For example, a mutant signal sequence from one strain of E. coli would be heterologous in a second E. coli strain if the second strain did not normally secrete any protein by the use of a signal having the nucleotide sequence of the mutant.

The preprotein gene generally is a mammalian preprotein, although it also includes DNA encoding fusions of microbial signal sequences with mature mammalian protein as well as microbial preproteins. This gene is to be heterologous in the transformed host, i.e. it is not normally transcribed or translated in the host that is selected. It may be heterologous prior to the introduction of the mutation, e.g. in the case of transformation of a bacterial cell with a mammalian preprotein, or only after the mutation, e.g. where a host preprotein is mutated and then used to transform the host.

The signal sequence prior to mutation desirably is homologous to the host cell. As such, it is ordinarily a signal that directs the secretion of a protein from the host cell. These proteins include cell membrane or periplasmic proteins such as the ST or heat stable enterotoxins of E. coli, AP or β-lactamase. Alternatively, the method herein is useful for evaluating the efficiency of secretion directed mutant by heterologous signal sequences, i.e., those which prior to mutation were not found in the host cell. Heterologous signal sequences may be those which had directed the secretion of the heterologous protein to be expressed, e.g. the HGH signal used with HGH or another heterologous protein, e.g. the proinsulin signal linked to HGH.

The method herein is most useful in evaluating the effect of mutations on protein secretion. Such mutations are generated in the host cell or in the DNA sequence encoding the heterologous protein, the signal used to direct secretion of the protein, or in the noncoding regions proximal to the signal. The advantage of the present method is that it is possible to use nonspecific mutagenesis, which is an economical technique, in order to create high-yielding host-vector systems and then to screen the resulting transformants for maximal levels of secreted fusion in order to identify these systems.

The mutations in the host cell are induced by well known methods, for example as have been employed for many years in enhancing the yields of amino acids or other secreted products. Typical agents include UV irradiation, mustard gas, nitrosoguanidine, 2-aminopurine, hydroxylamine and 5-Bromouracil.

The preprotein gene is preferably mutated at certain preselected regions or sites, termed target DNA. The preprotein gene comprises the promoter, Shine-Dalgarno, and intervening domains as well as a secretion signal sequence and the structural gene, which encodes either heterologous or fusion protein. The mutations are nucleotide insertions or deletions for increasing or decreasing, respectively, the spacing between or length of domains or substitutions, or are substitutions of base pairs. Insertions or deletions in the coding regions should net out as trimers in order to preserve the proper reading frame. The mutations in the coding regions are silent or expressed; silent mutations are those in which a nucleotide change is not expressed as an amino acid change because of the degeneracy of the genetic code, while expressed mutations appear as changes in the amino acid sequence.

The mutations in the transforming DNA, as opposed to the host cell genomic DNA, are introduced most economically by identifying the target DNA, excising a DNA fragment encompassing the identified target, mutagenizing the fragment in vitro and then religating the mutagenized fragment back into the DNA from which it was originally excised. Of course it is unnecessary to mutagenize the excised fragment per se, rather one only need mutagenize a fragment containing the same nucleotide sequence as the excised fragment. Ordinarily, the fragment will be exised at restriction enzyme sites that bracket the target region. If these sites are blunt-ended, mutagenesis of the target DNA at the restriction sites will not affect the ability of the target DNA to be religated into the remainder of the gene. If the sites do not form blunt-ended cells, but instead produce cohesive termini, it may be necessary after nonspecific mutagenesis to fill in the mutagenized single strands and blunt-end ligate a synthetic linker containing the desired restriction sites to the filled ends, retaining to the extent possible the proper reading frame. Some loss of mutagenized fragments is not critical because of the high efficiency of the screening process herein. Alternatively, and preferably, the whole plasmid containing the transforming DNA is mutagenized and then the target fragment excised by the bracketing restriction enzymes; only those target fragments are excised where mutations occur other than in the restriction sites. Again, the attendant recovery and screening of unmutagenized fragments does not unduly burden the method herein because of the high efficiency.

The degree of mutagenesis in this latter embodiment can be correlated with the loss of restriction sites. The appropriate degree of mutagenesis preferably will be that which results in partial digestion of the vector as is determined readily by the gel electrophoresis pattern of the digests, which also is used to recover target DNA from the digest for religation into unmutated vector. There is no need at this point to know the DNA sequences of the various mutagenized fragments; these sequences can be determined after high yielding mutants are identified. A convenient procedure is nitrous acid mutagenesis (12), although other methods for mutating DNA in vitro are known and acceptable.

The preprotein gene also may be mutated by synthesizing target DNA mutants having the desired sequences, including appropriate restriction sites or linkers that are used on conventional fashion to ligate the mutated DNA into the appropriate target site in the preprotein gene. The advantage of this sort of specific mutagenesis as opposed to nonspecific chemical methods is that no mutagen bias is encountered. i.e., one can be certain that all possible mutations have been evaluated in the screening assay and deletions or insertions are more readily accomplished. Furthermore, the preparation of synthetic DNA fragments is neither more expensive nor more time consuming than nonspecific mutagenesis for DNA targets below about 100 bp in length. Suitable methods for preparation of randomized or predetermined mutant target DNA and/or its insertion into vectors are described in the literature (36, 39, 9, 10, 11). Other suitable methods use M13 phage mutagenesis of the vector (28, 37, 38).

Silent mutations are introduced in order to select for host organism codon preference, to remove bases which when transcribed as mRNA would pair with other mRNA bases to form stem and loop structures that impede translation, or to achieve enhanced expression in other ways for which no theoretical basis has as yet been advanced (40). Silent mutations appear to act beneficially, if at all, at the level of expression rather than secretion. Furthermore, mutations that result in a change in an expressed amino acid in the signal sequence can result in improved levels of both expression and secretion. Both types of mutagenesis, silent and expressed, are optimally employed and improve the preprotein processing and secretion. An advantage of the present screening method is that it detects the cumulative effect of both silent and expressed mutations on expression and secretion. Preferably, silent mutations are induced within the first 20 to 30 base pairs of the preprotein coding region, while expressed mutations are made within DNA encoding the first 5 and/or last 5 amino acid residues in the signal domain. Expressed mutations also are made within the first about 10 residues of the mature protein, but these are less desirable than 5' noncoding or signal mutations because they result in a mutant final product. An advantage to making expressed mutations in signal sequences is that one potentially can accomplish both enhanced expression and enhanced secretion without modifying the primary structure of the mature protein product.

The mutated preprotein gene, present in a replicable vector, and under common control of expression and secretion with the marker protein, is used to transform host cells. The host cells are preferably bacterial cells having periplasmic spaces, but other bacterial or eukaryotic cells, including mammalian cells, are within the scope hereof. The host cell used for screening should not express and secrete a protein having marker protein activity which is indistinguishable from that of the marker protein, otherwise the host may create an excessive background. Such screening hosts are available in the art as marker-protein deficient mutants, or they are made by the using conventional transducing phage to introduce inactive deletion mutants of the marker protein into starting host cells.

The transformant cells are cultured and subcloned by suitable methods, e.g. colony plating or growth from single cell inocula in microtiter wells. The subcloning medium includes agents needed to develop or detect the change in marker polypeptide that occurs upon secretion. These agents include assayable enzyme substrates or such substrates plus an activating agent, e.g. a proteolytic enzyme, to be used with marker zymogens. In the case of alkaline phosphatase a convenient method uses semisolid media plated into a Petrie plate which contains chromogenic substrate for alkaline phosphatase. Active transformants are detected by the halo of hydrolyzed substrate, seen as the chromophore, released by the active marker enzyme that surrounds the colonies which are expressing and secreting the maximum amounts of marker. Similar substrates are used with beta-lactamase, and in preference to cell survival in the presence of penicillin because survival selection is an all-or-none response, rather than a quantitative assay of marker protein.

Transformants having the desired level of marker protein activity are selected from colony plates or microtiter wells, the transformants cultured and plasmid or vector DNA recovered. This DNA is digested to obtain the target mutagenized domain, purified, sequenced if desired and ligated into a vector encoding the preprotein gene containing the entire protein, but which protein is not fused to a marker protein. This construction then is used to transform permissive host cells, the cells cultured and the secreted mature desired protein recovered from the culture medium or peiplasmic space. The host cells used for expression need not be the screening host cells since the expression hosts can produce marker protein without affecting the expression and secretion of the desired protein. Surprisingly, the yields obtained with constructions containing the marker-preprotein fusion correlate well with yields obtained with the parallel unfused mutant preprotein gene.

Mutated host cells are screened in the process of this invention simply by obtaining an aliquot of a culture from a single cell isolated in turn from the mutated culture, transforming the cells in this aliquot with the marker-preprotein fusion, identifying those cultures which secrete the desired quantity of fusion and then transforming another aliquot of the selected culture with the unfused preprotein gene. The object of this procedure is to obtain the high yielding mutant hosts without contaminating fusion protein. However, this objective can be achieved by other methods. For example, the promoter used with the marker-preprotein fusion is selected to be active only upon induction. The mutant host cell containing this vector could still be used as a host for transformation by a vector bearing the mutant preprotein unfused to marker protein if translation of the preprotein vector is under the control of a constitutive promoter or one induced by a different mechanism than that of the promoter controlling the translation of the fusion.

In order to reduce the bulk of the Examples certain key words, phrases or designations are as defined or described below unless otherwise set forth in the Examples.

Plasmids are designated by a lower case p. The starting plasmids or vectors herein are commercially available, are publicly available on an unrestricted basis, or functionally equivalent plasmids are readily constructed from such available plasmids in accord with known procedures. In addition, other suitable plasmids or vectors are known in the art and will be apparent to the ordinary artisan.

"Digestion" of DNA refers to the catalytic cleavage of the DNA with an enzyme that acts only at certain locations in the DNA. Such enzymes are called restriction enzymes, and the sites for which each one is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 μg of plasmid or DNA fragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. Protein is removed from the incubation mixture by extraction with phenol and chloroform and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133–134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9: 6103-6114, and D. Goeddel et al., 1980, "Nucleic Acids Res." 8: 4057.

"Transformation" means introducing DNA into an organism so that the DNA is replicable, either as an extrachromosomal element or chromosomal integrant. Unless otherwise provided, the method used herein for transformation of *E. coli* is the $CaCl_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90, may be used.

"Oligonucleotides" are short length single or double stranded polydeoxynucleotides which are chemically synthesized by known methods and then purified on polyacrylamide gels.

EXAMPLE 1

*E. coli* K12 strain 294 (13) was used for all plasmid constructions. All plasmids were replicated in this strain except when it was necessary to digest the resulting plasmid with BclI. *E. coli* strain GM48 (14) was used in such cases. The alkaline phosphatase screening method necessitated the use of an *E. coli* strain which produced no alkaline phosphatase. The *E. coli* strain MZ-9 (15) was used for this purpose. Another suitable phoA deletion strain of *E. coli* is described (41) and available through the *E. coli* Genetic Stock Center. Strain YK514 (35) also is useful. The starting plasmids pHI-1 (6), pMC1403 (1), pPreHGH207-2 (8), and pHGH207-1 (16) have all been previously described.

Restriction digests were performed using commercial enzymes. The enzymes were used as directed by the suppliers. The Klenow fill-in reactions, ligations and transformations were performed according to the methods outlined in Maniatis et al. (17).

The deoxyoligonucleotide was synthesized on a Biosearch SAM synthesizer using phosphoamidite chemistry (18,19). DNA sequencing was performed using the dideoxy method on M13 single-stranded phages (20).

The X-P MOPS plates used to screen for alkaline phosphatase overproducing colonies were prepared as previously reported (6). Alkaline phosphatase (21), β-galactoside (22), and β-lactamase enzyme assays (23) were performed as reported. The fractionation of periplasmic material from cytoplasmic material utilized the osmotic shock procedure (24).

The nitrous acid mutagenesis was performed as previously reported (12) with the following modifications. 20 µg of PreHGHBam-AP was treated in 250 µl of 250 mM sodium acetate (pH 4.7), 0.2 mM spermidine using variable concentrations of sodium nitrite. The concentrations were 0, 70 mM, 210 mM, and 630 mM. The reactions were performed at 32° for 16 hr and then neutralized with 100 µl 1M Tris-HCl (pH 8). The reactions were ethanol precipitated twice from 3M NaOAc pH 5.4 and then digested with XbaI and BamHI. The resulting digests were subjected to preparative gel electrophoresis on an 8 percent acrylamide gel and the 78mer bands were electroeluted (12). The isolated fragments were ligated by standard procedures (17).

Construction of HGH-AP Fusions

It was necessary to determine whether a HGH-AP fusion would have phosphatase enzymatic activity and if periplasmic secretion was necessary for activity. In order to test this, the analogous plasmids pPreHGH-AP and pMetHGH-AP (FIG. 1) were constructed. These plasmids were identical except for the sequence immediately following the ATG initiation codons. pPreHGH-AP had the DNA sequence coding for both the signal sequence and the structural gene for HGH. pMetHGH-AP only had the structural gene following the initiation codon. In both plasmids the expression of the fusion proteins is the result of transcription from an *E. coli* tryptophan (trp) operon promoter and translation initiation utilizing a ribosome binding site from the trp operon leader gene (16).

The source of the alkaline phosphatase gene was pHI-1 (6). A 2.2 kb BclI to XhoI fragment codes for most of the structural gene for alkaline phosphatase, as well as containing 3' untranslated sequence. Isolation of this fragment deletes all of the signal sequence and 70 bp of the structural gene (25). This fragment was cloned into a vector derived from pMC1403 (1), a plasmid containing β-gal with a polylinker preceding that gene. The β-gal gene was replaced with the AP gene by first filling in both the XmaI and BclI sites with Klenow and dNTPs, restoring the XmaI/SmaI site. The plasmid pXMA-AP was useful as an intermediate in that it allowed for the flexibility of shifting the AP gene to all three reading frames by digesting with XmaI and treating with $S_1$, digesting with XmaI and filling in with Klenow and dNTPs, or digesting with SmaI.

A convenient site in the HGH gene for a fusion junction was the PvuII site located just 10 bases from the termination codon. By utilizing the PvuII site (a blunt end cutter) for the fusion junction, it is necessary to cleave pXMA-AP with XmaI and fill-in with Klenow to obtain a fusion in which the HGH and AP are in frame (see FIG. 1). The fusions were constructed by a three-way ligation of a Pst-Pst fragment bearing the trp promoter and 5' end of the HGH gene derived from either pPreHGH207-2 or pHGH207-1, a PstI-PvuII fragment bearing the 3' end of the HGH gene from pHGH207-1 and a Xma-Pst vector bearing the gene for alkaline phosphatase (FIG. 1).

The resulting plasmids were transformed into AP⁻ strain and plated on X-P MOPS plates. Only pPreHGH-AP resulted in blue colonies, indicating AP activity, while pMetHGH-AP and a pBR322 control resulting in white colonies. Alkaline phosphatase assays on stationary phase cultures of such bacteria were done to confirm the plate assays. pPreHGH-AP showed easily detectable levels of AP, while pMetHGH-AP showed no detectable activity compared to the pBR322 negative control (Table 1). Cell extracts of the cultures harboring pPreHGH-AP and pMetHGH-AP were subjected to western blot analysis (26) using an antibody against HGH as a probe. Both plasmids directed the synthesis of a HGH fusion protein of the proper size. The cultures carrying pMetHGH-AP produced significantly more fusion protein relative to those carrying pPreHGH-AP, but it was completely devoid of AP activity. The conclusion was that the fusion protein is active when secreted and not active when it remains intracellular.

Introduction of BamHI Site

The mutagenesis approach used in this Example required unique restriction sites flanking the signal sequence. Previous constructions (8,16) had generated a unique Xba site preceding the initiation ATG, but no unique site existed at the 3' end of the DNA coding for the signal peptide. It was desirable to engineer a site within the signal region rather than the beginning of the mature gene because the latter could result in mutations within the mature coding sequence and consequently the expression of a different mature protein. Examination of the protein sequence of the signal revealed the opportunity to engineer a unique BamHI site at the 3' end of the signal coding sequence based on the degeneracy of codons for the amino acids.

Traditional methods for oligonucleotide site-directed mutagenesis were utilized (27,28). An XbaI-PstI fragment bearing the DNA coding for the signal sequence was cloned into MP11 and single-stranded phage DNA was isolated. A 30 base pair oligonucleotide, 5' TGGCTTCAAGAGGGATCCGCCTTCCCAACC, was synthesized and used as the primer for the mutagenesis. After transfection, screening by plaque hybridization, and sequencing of the positive clones, a clone was identified bearing the desired mutation, namely introduction of a BamHI site and the preservation of the amino acid sequence of the signal peptide.

The DNA from this M13 phage was isolated as its double stranded intracellular form and digested with XbaI and PstI. The small fragment was ligated to restore the trp promoter HGH-AP fusion construction that now had the unique BamHI site positioned at the 3' end of the signal sequence. The plasmid was transformed into the MS-9 (AP⁻) strain and single colonies grown to stationary phase in Luria Broth. These cultures were assayed for alkaline phosphatase activity and compared to cultures bearing the fusion plasmid previous to the incorporation of the BamHI site (Table 1). The introduction of the BamHI site results in a small decrease in AP activity. It was encouraging to note that this small difference in activity could be detected on the X-P MOPS plates by a difference in the blue coloration of the colonies. The plate screening system thus appeared to be sensitive enough to detect small phenotypic changes.

Nitrous Acid Mutagenesis and Colony Screening

The nitrous acid mutagenesis was performed in a similar fashion to that previously reported (5) except that whole plasmid was treated with nitrous acid and subsequently digested with restriction enzymes. The concentration of mutagen affected the efficiency of the restriction digest with XbaI and BamHI. Digestion of DNA treated with 630 mM nitrite resulted in virtually no 78 bp fragment. Concentrations of 70 and 210 mM nitrite resulted in partial digestion and the 78 bp XbaI-BamHI fragment was isolated by gel electrophoresis and electroelution. Nonmutagenized vector was prepared by restricting preHGHBam-AP with XbaI and BamHI and purifying the large fragment by gel electrophoresis and electroelution. The mutagenized fragments and the vector were then ligated, transformed into AP⁻ cells and plated on X-P MOPS plates.

Approximately 200 colonies were derived from the 210 mM nitrite treated fragment and about 600 from the 70 mM nitrite reaction. A control consisting of ligation of nonmutagenized 78mer and vector resulted in approximately 5000 colonies. These plates were examined for intensely blue colonies and eight colonies derived from the 210 mM nitrite mutagenesis treatment showed a more intense blue color while none were noted on the other plates. These eight colonies were purified by streaking and stationary phase cultures grown. Alkaline phosphatase assays confirmed the enhanced expression and secretion of the fusion protein in six of the cases.

The DNAs coding for the signal sequences of these plasmids were sequenced by subcloning the XbaI-BamHI 78mer piece into M13mp9 and performing dideoxy sequencing (20). The results are presented below.

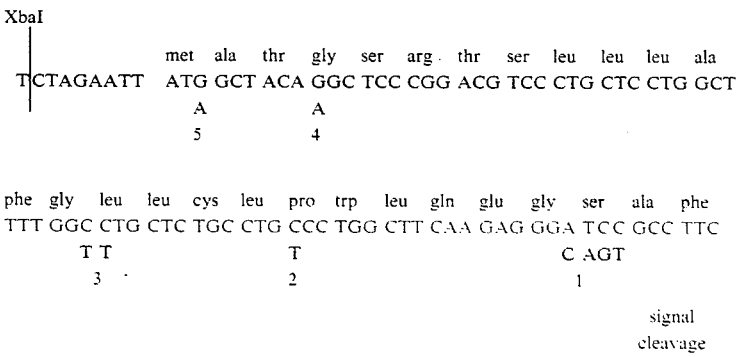

The letters below the DNA sequence depict the base substitutions represented by the mutation number below the letter. In all cases, mutations were found in the targeted signal sequence. Out of the six sequenced, one mutation appeared three times, resulting in only four distinct isolates. The possibility that mutations outside of the target region were responsible for the observed phenotype was excluded by recloning the mutant XbaI-BamHI 78mer fragments into nonmutagenized vector. The phenotypic results were the same.

The critical question existed as to whether these signal mutations would result in the enhanced expression and secretion of HGH when transferred into an expression plasmid for HGH. The mutations were transferred into pPreHGH207-2 by digesting with PstI and isolating the large vector fragment. The mutant PreHGH-Bam-AP plasmids were digested with PstI and the small fragment isolated. Ligation of both pieces, transformation with AP− cells and plating on LB amp plates resulted in colonies whose correct plasmid construction was confirmed by restriction analysis. Colonies of each mutant were grown to stationary phase in L.B. and sonicated cells were assayed for HGH by a radioimmune assay (RIA) (13). The relative levels are reported in Table 1.

TABLE 1

Phenotype of Isolated Mutants

| Mutant Description | Relative AP levels when expressing HGH-AP fusion[1] | Relative HGH levels when expressing HGH[2] |
| --- | --- | --- |
| pBR322 | .06 ± .01 | <.01 |
| pMetHGH-AP/ pHGH207-1 (no signal) | .07 ± .01 | 14 |
| pPreHGH-AP/ pPreHGH207-2 (wild type signal) | 1 | 1 |
| Mutant 1 (engineered BamHI site) | .7 ± .05 | .5 |
| Mutant 2 (Pro → Leu, amino acid 19) | 2.0 ± .1 | .8 |
| Mutant 3 (no amino acid change) | 2.0 ± .2 | 7.5 |
| Mutant 4 (Gly → Asp, amino acid 4) | 2.7 ± .2 | 3.0 |
| Mutant 5 (Ala → Thr, amino acid 2) | 2.6 ± .3 | 4.5 |

[1]Value of 1 equals .05 units ± .003 units of AP as previously defined (21).
[2]Value of 1 equals 105 ng of HGH/OD$_{550}$ of cells.

The assay used for Table 1 measured total HGH expressed. In order to differentiate between cytoplasmic and periplasmic HGH osmotic shock cellular fractionation (24) was performed on stationary phase cultures containing the mutant and wild type signals. A culture producing cytoplasmic metHGH (13) was included as a control. The RIA results are reported in Table 2, along with a cytoplasmic marker protein β-galactosidase and a periplasmic marker protein β-lactamase.

TABLE 2

Localization of HGH in mutants secreting native HGH

| Plasmid Description | HGH in periplasm (pct. of total) | β-lactamase in periplasm (pct. of total) | β-galactosidase in periplasm (pct. of total) |
| --- | --- | --- | --- |
| pPreHGH207-2 (wild type) | 66 | 90 | 8 |
| Mutant 2 Pro → Leu | 57 | 91 | 5 |
| Mutant 3 no amino acid change | 80 | 90 | 8 |
| Mutant 4 Gly → Asp | 66 | 90 | 6 |
| Mutant 5 Ala → Thr | 54 | 92 | 9 |
| pHGH207-1 (mature) | 20 | 88 | 7 |

These results demonstrate that the majority of heterologous protein being produced was being exported to the periplasm and the isolated mutations result in enhanced expression and periplasmic secretion of the protein.

The distinctive feature of the HGH-AP fusions is the selectivity of the AP enzymatic activity for a fusion protein that has been exported to the periplasmic space. Alkaline phosphatase is known to be active only as a dimer and the disulfide bond forming dimerization process requires the oxidizing environment of the periplasm (5). In this model system the fusion protein appears to be behaving in a similar manner.

Four distinct mutations in the region of the gene coding for the signal peptide are described in this Example. It is notable that the mutation which results in the greatest increase of expression and secretion (no. 3 in Table 1) does not produce a change in the amino acid sequence of the signal peptide. This double mutation is believed to result in enhanced translation, which in turn results in enhanced secretion. The double helical regions of a messenger RNA surrounding the initiation ATG have been implicated in the efficiency of translation initiation and consequently the expression levels of the protein product (29). However, secondary structure computer analyses of the predicted message (30) shows no substantial difference as compared to the wild type sequence. Mutation 3 involves the conversion of a GGC codon for glycine into GGT and a CTG codon for leucine into TTG. The E. coli preference codons for leucine are CTC, TTA, CTA or CTT (Table I, reference 42). Accordingly, mutation 3 does not effect the conversion of a leucine non-preference codon into an E. coli preference codon. Therefore, a method is provided for enhancing the expression and secretion of a heterologous preprotein from transformed cells comprising introducing a plurality of silent mutations into the signal sequence of the preprotein and thereafter screening the transformants for secretion of heterologous protein, provided that such mutations do not (a) change a codon from one not preferred by the host cell into one that is so preferred or (b) result in a substantial change in any secondary messenger structure present in transcripts of the preprotein.

Host cell preference codons, e.g. for E. coli, are well known. These codons have been identified by analyzing the codons used by a given species to encode a particular amino acid residue. Some codons on balance are preferred over others, and it is now known to select these preferred codons to enhance expression in heterologous hosts (42). Avoidance of secondary messenger structure by codon selection is accomplished by known methods (30) which involve calculating the energy levels of potential intramolecular complementarity and using codons that minimize such complementarity (43).

The other three mutations are less dramatic. The most curious one is number 4 (gly4→asp4). This change to a negatively charged amino acid in the amino terminus of the signal is counter to the trend normally observed in signal peptides in E. coli (31). Again, it is possible that what is being observed is an effect on expression and that the mutation is merely not deleterious to the secretion process. This is plausible because this mutation occurs near the initiation ATG and is well within the region known to be important for ribosome initiation on messenger RNA (30).

Nitrous acid mutagenesis was effective in the generation of interesting mutations. This method, however, suffers from several limitations. Nitrous acid is capable of A to G and C to T changes on both the coding and noncoding strands of DNA. This results in the possibility of every base pair being mutated, but to only one possible mutation. Hence T can be mutated to C by virtue of deaminating the A with which it is base paired. Similarly, G can be mutated to A. This results in only one-third of the possible mutations.

A secondary difficulty with nitrous acid mutagenesis is that it damages DNA in more ways than just deaminating the heterocyclic bases. This leads to a loss of biological activity and results in lowered efficiency of digestion with restriction enzymes, ligation and transformation, leading in turn to difficulties in generating large numbers of potentially mutagenized transformants.

A third problem that is suggested is one of hot spot mutagenesis. Mutant number 3 was isolated three times out of a sample of six. While it is conceivable that this was due to siblings resulting in the transformation procedure, it is unlikely, and a more likely explanation is hot spot mutagenesis. Accordingly, the randomized trimer method of Hui et al. preferably should be employed (36).

One curious property of the isolated mutants is that the phenotypic differences between the wild type and the mutants were greater when the protein being secreted was HGH versus the HGH-AP fusion. This is possibly explained by the fact that strains transformed with the mutant plasmids, especially number 4, grew significantly slower than strains carrying the parental plasmid when expressing the HGH-AP fusion. This effect on growth is far less noticeable in the case where the mutants are expressing HGH. Such a growth inhibiting effect of high levels of the HGH-AP fusion could be a problem when exploring for mutations that lead to higher levels of expression and secretion of fusion protein. In such cases it is suggested that one use a weaker promoter or introduce a trp repressor gene to lower the steady-state messenger RNA levels.

All literature citations in the following bibliography and elsewhere herein are expressly incorporated by reference.

Bibliography

1. Casadaban, M. J., Chon, J. and Cohen, N. (1980) J. Bact. 143, 971-980.
2. Casadaban, M. J. and Cohen, S. N. (1980) J. Mol. Biol. 138, 179-207.
3. Guarente, L., Lauer, G., Roberts, T. M. and Ptashne, M. (1980) Cell 20, 543-553.
4. Palva, E. T. and Silhavy, T. J. (1984) Mol. Gen. Genet. 194, 388-394.
5. Michaelis, S., Inouye, H., Oliver, D., and Beckwith, J. (1983) J. Bacteriol. 154, 366-374.
6. Inouye, H., Michaelis, S., Wright, A. and Beckwith, J. (1981) J. Bacteriol. 146, 668-675.
7. Wright, A., Hoffman, C. and Fishman, Y. (1983) J. Cell. Biochem. Supplement 7B, 346.
8. Gray, G. L., Baldridge, J. S., Heyneker, H. L., and Chang, C. N., Nucleic Acids Research, submitted.
9. Weiher, H. and Schaller, H. (1982) Proc. Natl. Acad. Sci. U.S.A. 79, 1408-1412.
10. Shortle, D., Grisafi, P., Benkovic, S. J. and Botstein, D. (1982) Proc. Natl. Acad. Sci. U.S.A. 79, 1588-1592.
11. Matteucci, M. D. and Heyneker, H. L. (1983) Nucleic Acids Research 10, 3113-3121.
12. Warburton, N., Boseley, P. G. and Porter, A. G. (1983) Nucleic Acids Research 11, 5837-5854.
13. Goeddel, D. V., Heyneker, H. L., Hozumi, T., Arentzen, R., Itakura, K., Yansura, D. G., Ross, M. J., Miozzari, G., Crea, R. and Seeburg, P. H. (1979) Nature 281, 544-548.
14. Marinus, M. G. and Norris, N. R. (1973) J. Bacteriol. 114, 1143.
15. Inouye, H., Pratt, C., Beckwith, J. and Torriani, A. (1977) J. Mol. Biol. 110, 75-87.
16. de Boer, H. A., Comstock, L. J., Yansura, D. G. and Heyneker, H. L. (1982) In: Promoters: Structure and Function, R. L. Rodriguez and M. J. Chamberlin (eds.) Praeger, New York, pp. 462-481.
17. Maniatis, T., Fritsch, E. F. and Sambrook, J. In: Molecular Cloning, A Laboratory Manual, Cold Spring Harbor Laboratory, New York, pp. 98-147.
18. Matteucci, M. D. and Caruthers, M. H. (1981) Journal Am. Chem. Soc. 103, 3185-3189.
19. Beaucage, S. L. and Caruthers, M. H. (1981) Tet. Letters 22, 1859-1862.
20. Sanger, F., Nicklen, S. and Coulson, A. R. (1977) Proc. Natl. Acad. Sci. U.S.A. 74, 5463-5467.
21. Brickman, E. and Beckwith, J. (1975) J. Mol. Biol. 96, 307-316.
22. Miller, J. H. (1972) In: Experiments in Molecular Genetics, Cold Spring Harbor Laboratory, New York, pp. 356-359.
23. Jones, P. W., Wilson, H. W. and Novick, Jr., W. J. (1982) J. Clin. Microbiol. 15, 677-683.
24. Koshland, D. and Botstein, D. (1980) Cell 20, 749-760.
25. Kikuchi, Y., Yoda, K., Yamasaki, M. and Tamura, G. (1981) Nucleic Acids Research 9, 5671-5678.
26. Burnette, W. W. (1981) Anal. Biochem. 112, 195-203.
27. Winter, G., Fersht, A. R., Wilkinson, A. J., Zoller, M. and Smith, M. (1982) Nature 299, 756-758.
28. Adelman, J. P., Hayflick, J. S., Vasser, M. and Seeburg, P. H. (1983) DNA 2, 183-193.
29. Gold, L., Pribnow, D., Schneider, T., Shinedling, S., Singer, B. S. and Stormo, G. (1981) Annual Review of Microbiology.
30. Tinoco, I., Borer, P. N., Dengler, B., Levine, M. D., Uhlenbech, O. C., Crothers, D. M. and Gralla, J. (1973) Nature New Biol. 246, 40-41.
31. Perlman, D. and Halvorson, H. O. (1983) J. Mol. Biol. 167, 391-409.
32. Guarante, L. et al., U.K. Patent Application 2,071,671.
33. Gilbert, W. et al., U.S. Pat. No. 4,411,994.
34. Gilbert, W. et al., U.S. Pat. No. 4,338,397.
35. European Patent Application 77,569.
36. Hui, A. et al., "The EMBO Journal" 3(3): 623-629 (1984).
37. U.K. Patent Application 2,130,219A.
38. Winter, G. et al., (1982) Nature 299, 756-758.
39. Wallace, R. et al., (1981) Nucleic Acids Research 9(15), 3647-3656.

40. Tessier, L. -C. et al., (1984) Nucleic Acids Research 12(20), 7663–7675.
41. Sarthy, A. et al., (1981) J. Bact. 145, 288–292.
42. U.S. Pat. No. 4,356,270.
43. EP 75,444A.

I claim:

1. A method for producing a secreted protein comprising (a) providing a replicable expression vector comprising nucleic acid that encodes a marker protein and nucleic acid that encodes a preprotein gene capable of expression and secretion of the preprotein, said marker protein undergoing a detectable change in activity upon secretion of said marker protein from a host cell, and said marker protein being fused to the C-terminus of the preprotein and being capable of expression and secretion under common control; (b) preparing a plurality of said vectors each containing a mutation in the preprotein gene; (c) transforming a host cell with each vector of step (b) wherein the mutated preprotein genes of step (b) are heterologous to said host cell; (d) assaying the transformed host cells for a change in activity which occurs in the marker protein upon secretion of said marker protein; (e) selecting the transformed host cell capable of secreting the most fused protein product; (f) introducing the mutation identified in step (e) into a vector comprising the selected, heterologous preprotein gene unfused to the marker protein nucleic acid; (g) transforming a host cell therewith; and (h) recovering said secreted protein from the host cell of step (g) in culture.

2. The method of claim 1 wherein the marker protein is amino terminal deleted so as to not substantially interfere with the biological activity of the marker protein.

3. The method of claim 1 wherein the marker protein is a proenzyme or zymogen and the activated marker protein is a protein having enzymatic activity.

4. The method of claim 1 wherein the host cell is a mammalian or vertebrate cell.

5. The method of claim 1 wherein the preprotein is a mammalian protein.

6. The method of claim 1 wherein said mutation in step (b) is a silent mutation.

7. The method of claim 1 wherein said mutation in step (b) is an expressed mutation.

8. The method of claim 1 wherein the preprotein is a mammalian protein and the host cell is a bacterial cell having a periplasmic space.

9. The method of claim 1 wherein the marker protein is alkaline phosphatase.

10. The method of claim 1 wherein additionally in step (e) determining the DNA sequence of the mutation in the vector from step (b).

11. The method of claim 1 wherein the DNA sequence of the vector mutation in step (b) is determined by synthesizing vector DNA of a known sequence.

* * * * *